United States Patent [19]

Lichtenauer

[11] Patent Number: Plant 7,590

[45] Date of Patent: Jul. 16, 1991

[54] APPLE TREE - RUBINSTAR VARIETY

[76] Inventor: Joachim Lichtenauer, D-6901 Gaiberg, Fed. Rep. of Germany

[21] Appl. No.: 454,063

[22] Filed: Dec. 20, 1989

[51] Int. Cl.[5] ..... A01H 5/00

[52] U.S. Cl. ..... Plt./34

[58] Field of Search ..... Plt./34

[56] References Cited

U.S. PATENT DOCUMENTS

P.P. 5,937 4/1987 Morren-De Coster ..... Plt. 34
P.P. 6,148 4/1988 Ligonniere ..... Plt. 34
P.P. 7,146 2/1990 Schneider ..... Plt. 34

*Primary Examiner*—James R. Feyrer

*Attorney, Agent, or Firm*—Burns, Doane, Swecker & Mathis

[57] ABSTRACT

A new and distinct variety of apple tree is provided which forms quality fruit having an attractive substantially uniform red coloration. The new variety originated in the Federal Republic of Germany as a mutation of the Jonagold variety. The fruit of the new variety can be distinguished from that of its mother variety by the exhibition of a more intense red coloration which covers a greater portion of the fruit surface in the substantial absence of striping. Also, the new variety forms fruit which colors approximately one week earlier than its parent. Such improved fruit coloring propensity is deemed to be of substantial commercial importance.

4 Drawing Sheets

SUMMARY OF THE INVENTION

The new variety of the present invention resulted as a bud mutation of the Jonagold variety. Such Jonagold variety was introduced in 1968 by Roger Way of the New York State Agricultural Experiment Station, Geneva, N.Y.

The bud mutation of the present invention was discovered by me 1980 at Gaiberg, Federal Republic of Germany. It was observed that an apple on a single spur exhibited a highly attractive more intense red coloration than other apples formed on the same tree growing in the orchard near my home. Competing branches were removed in order to enable this distinctive spur to grow to its fullest potential. As a branch developed from the spur, it was observed that it continued to bear attractive apples that were significantly more colored and earlier coloring than other apples formed on the same tree. Had I not discovered and preserved this new variety it would have been lost to mankind.

The new variety bears apples which (1) exhibit attractive red coloration over a greater proportion of the surface than the Jonagold variety with approximately 70 to 90 percent of the surface being red, (2) are of a more intense red coloration than the Jonagold variety, and (3) color approximately one week earlier than the Jonagold variety. Such apple coloration of the new variety appears as a blush in the substantial absence of striping as is exhibited by the Jonagold variety. Also, the new variety exhibits a slightly more compact growth habit than the Jonagold variety and its other previously reported mutations. In all other respects the new variety exhibits characteristics which are substantially identical to those of the Jonagold variety.

During 1983 buds from the sported branch were grafted asexually onto M9 rootstocks. Trees resulting from this budding were found to exhibit the same distinctive fruit characteristics as the original mutated branch. Subsequent propagations by me at Gaiberg, Federal Republic of Germany, and by personnel of Herr Nurseries at Meckenheim, Federal Republic of Germany, have further confirmed that the distinctive characteristics of the new variety are stably and reliably transmitted to the third generation.

The new variety has been named the Rubinstar variety. Since 1987 trees of this new variety have been marketed in Europe by Herr Nurseries of Meckenheim, Federal Republic of Germany. No trees of the new variety have been marketed in the United States prior to the filing date of this Application.

BRIEF DESCRIPTION OF THE PHOTOGRAPHS

The accompanying photographs show typical specimens of the new variety in color as nearly true as is reasonably possible to make the same in a color illustration of this character. The photographs were obtained at the Federal Republic of Germany.

Figure 1:
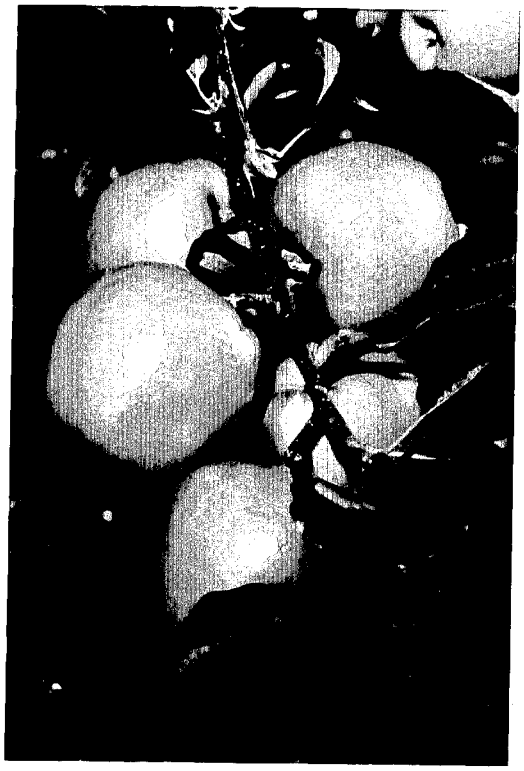
FIG. 1 illustrates typical specimens of the foliage and fully-colored fruit of the new variety while present on the tree.
Figure 2:
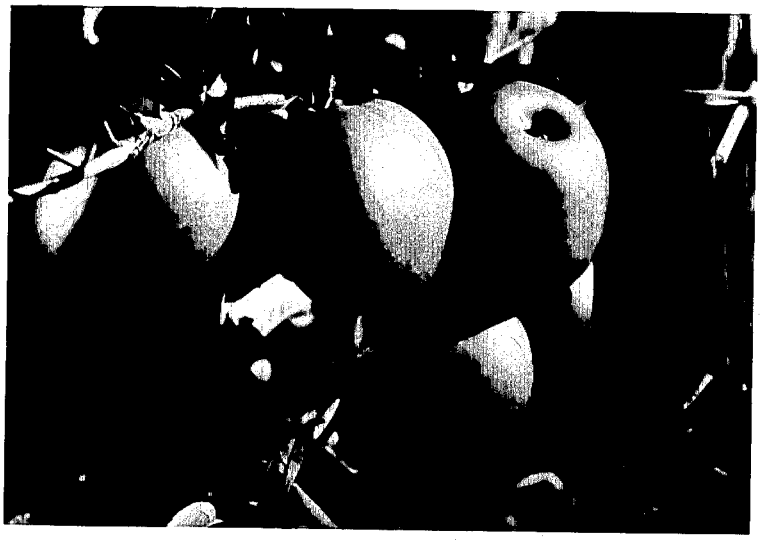
FIG. 2 illustrates additional typical specimens of the foliage and fully-colored fruit of the new variety while present on the tree.
Figure 3:
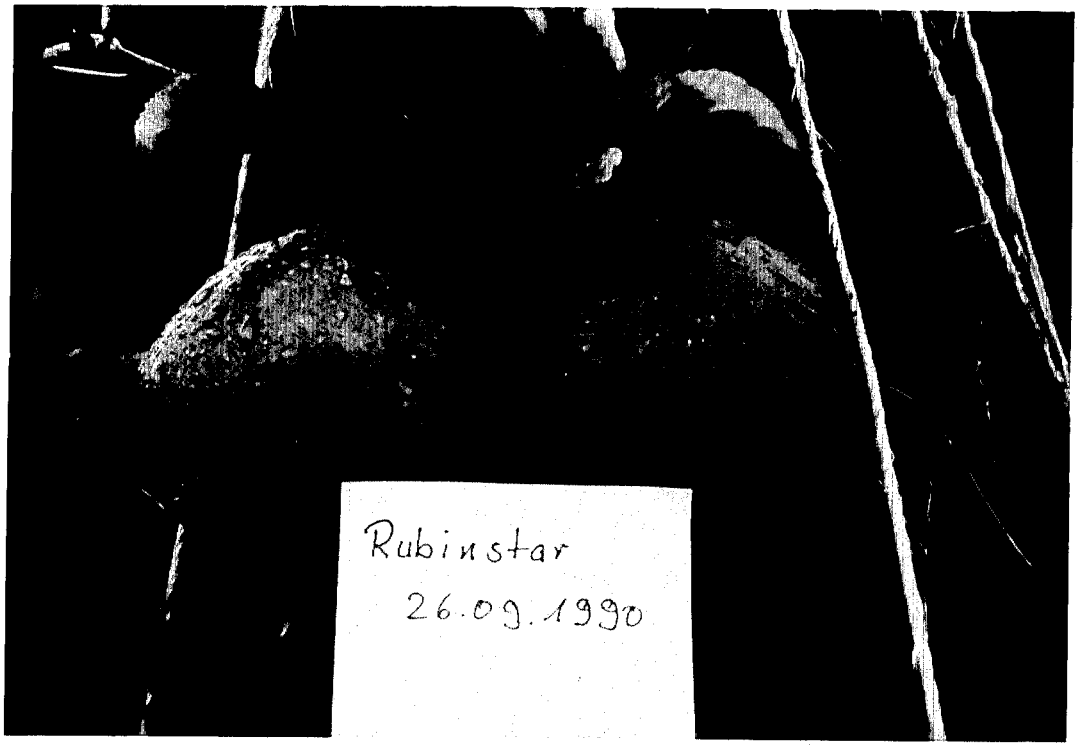
FIG. 3 illustrates the typical coloration of the fruit of the new variety on Sept. 26, 1990 while present on the tree at Gaiberg. It will be noted that the fruit bears an intense red coloration in the substantial absence of striping.
Figure 4:
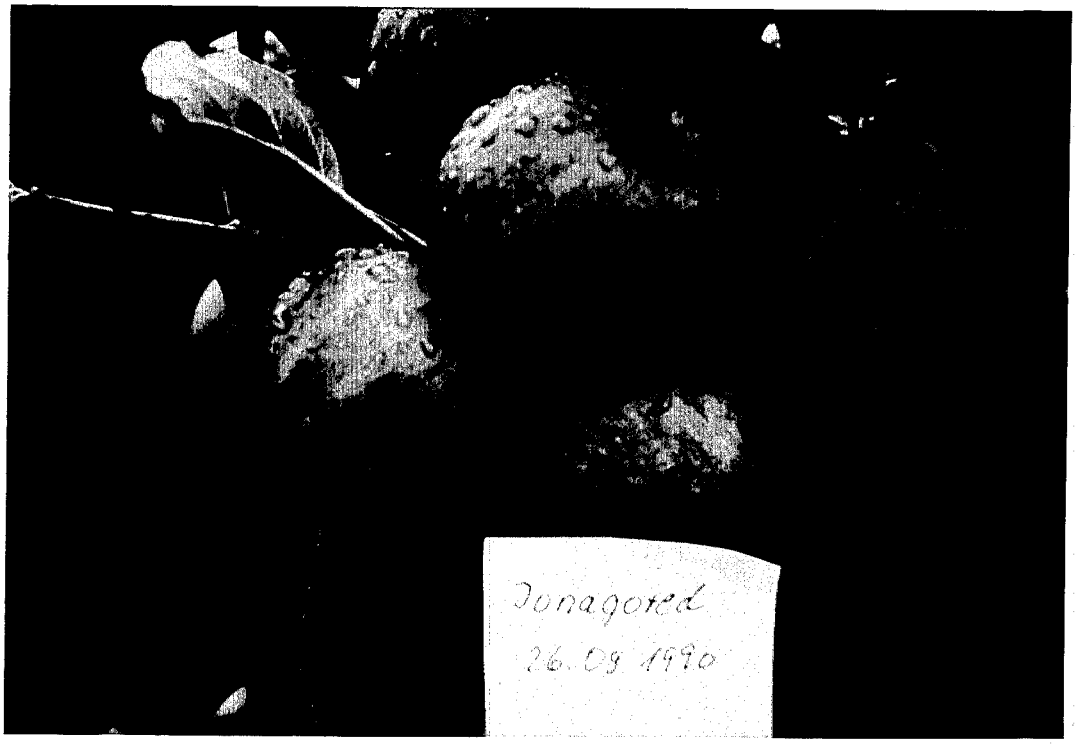

FIG. 4 illustrates for comparative purposes the typical coloration of the fruit of the earlier reported mutation of U.S. Plant Pat. No. 5,937 on Sept. 26, 1990 while present on a tree at Gaiberg when subjected to the same growing conditions as the tree of FIG. 3. It will be noted that the fruit of this mutation exhibits striping which is not as clearly illustrated in the photographs of U.S. Plant Pat. Nos. 5,937 and 7,146 (FIGS. 10 and 11).

Figure 5:
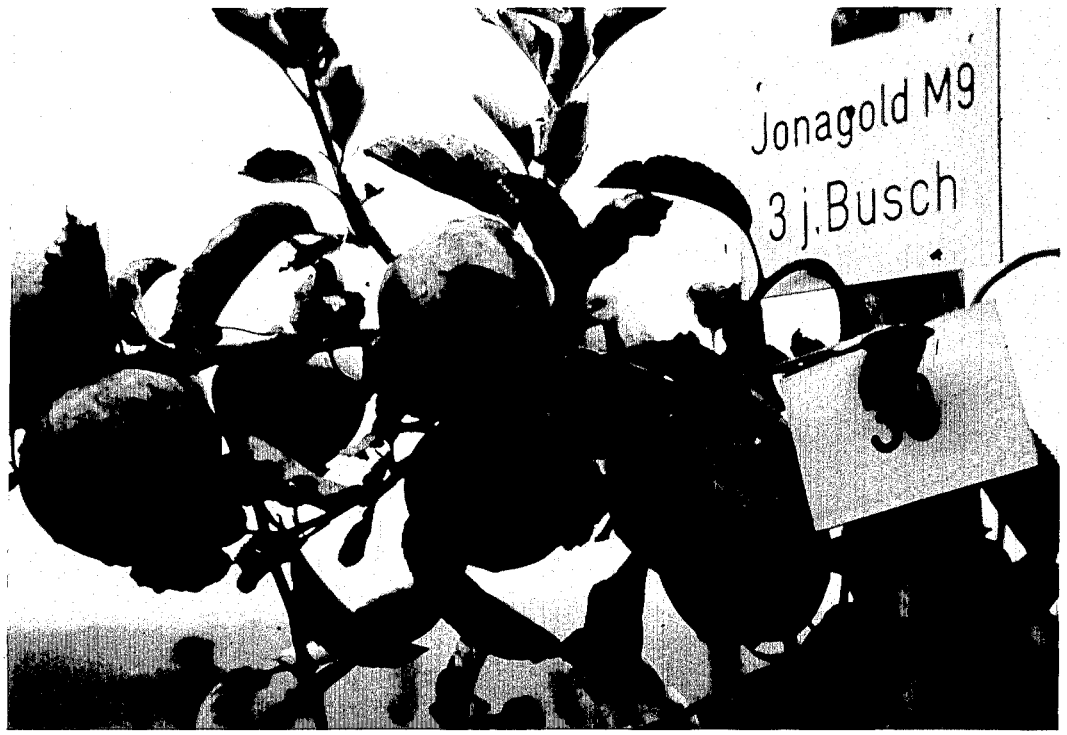

FIG. 5 illustrates for comparative purposes the typical coloration of the fruit of the mother Jonagold variety on Sept. 26, 1990 when subjected to the same growing conditions as the tree of FIG. 3. The considerably lesser coloration of the fruit when compared to that of the new variety is apparent.

Figure 6:
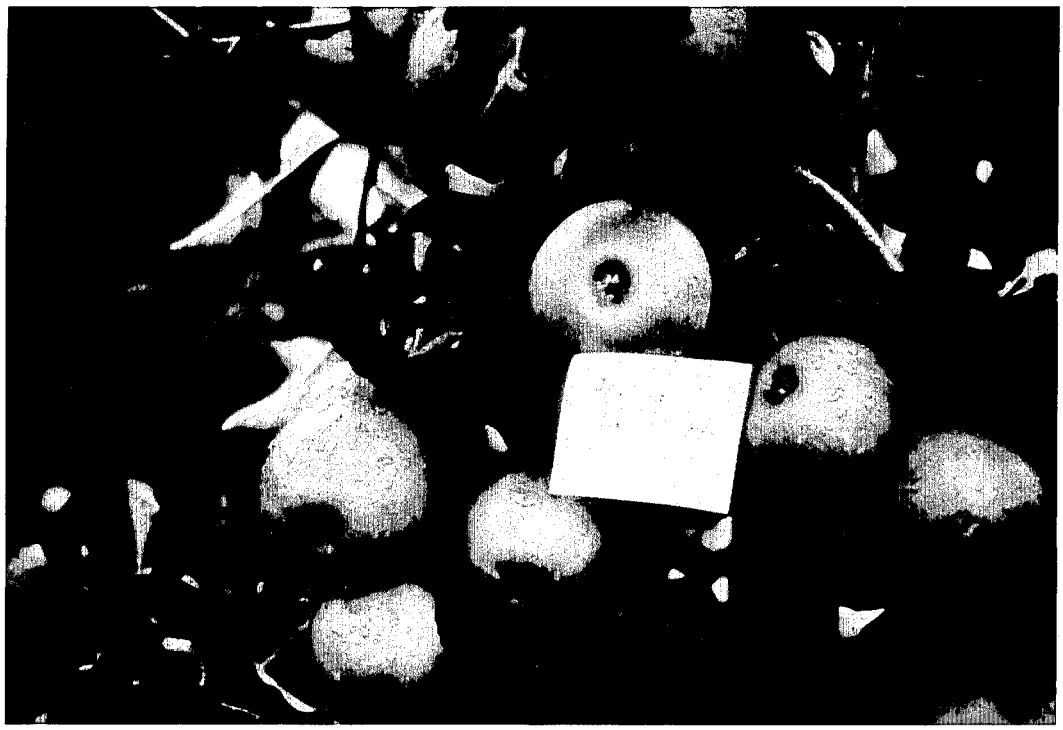

FIG. 6 illustrates for comparative purposes the coloration of the fruit of the Schneica variety (U.S. Plant Pat.

No. 7,146) on Sept. 26, 1990 when subjected to the same growing conditions as the tree of FIG. 3. The considerably lesser coloration of the fruit when compared to that of the new variety is apparent.

Figure 7:
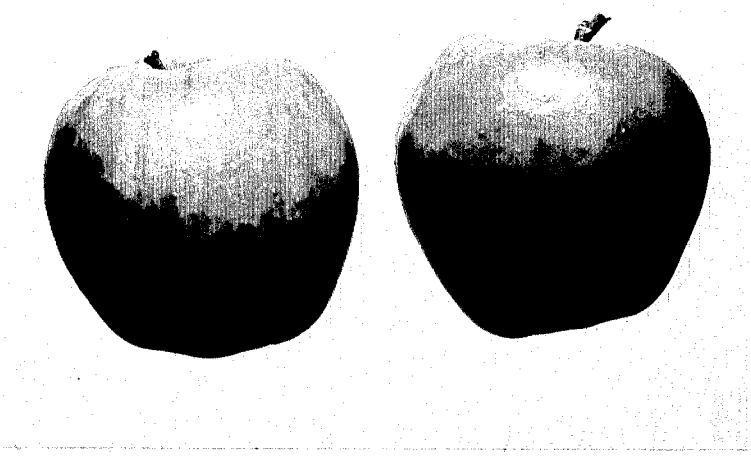

FIG. 7 illustrates for comparative purposes side views of typical fully-colored fruits of the mutation of U.S. Plant Pat. No. 5,937 on the left and the new variety on the right. It will be noted that the fruit on the left exhibits typical striping while the fruit of the new variety exhibits an attractive more uniform red coloration.

DETAILED DESCRIPTION

The observations described hereafter were made of trees growing at Gaiberg and Meckenheim, Federal Republic of Germany.

Characteristics, such as tree vigor, bloom period, crop yield, disease resistance, and insect resistance, are substantially identical to those of the Jonagold variety. Also, the fruit of new variety exhibits substantially the same shape, size, flesh characteristics, flavor, and configuration variability, as the Jonagold variety. The growth habit of the new variety tends to be slightly more compact than that of the mother Jonagold variety and its previously reported mutations.

As previously indicated, the fruit coloration of the new variety is different that that of the Jonagold variety as well as that of the earlier reported mutations of U.S. Plant Pat. Nos. 5,937, 6,148 and 7,146. Such red coloration is more intense and of a brighter and purer red than the mother Jonagold variety and its earlier reported mutations. For instance, the red coloration covers more of the surface than the coloration present on the fruit of the Jonagold variety even on the shaded inside of the tree with approximately 70 to 90 percent of the surface commonly assuming such coloration on an average year. The new variety exhibits a brighter and truer red fruit coloration than that of the browner red fruit coloration of the variety of U.S. Plant Pat. No. 5,937. The intense red fruit coloration of the new variety develops as a blush while the coloration of the mutation of U.S. Plant Pat. No. 5,937 tends to develop in a striped pattern. It is recognized by those who are well familiar with the mutation of U.S. Plant Pat. No. 5,937 that it forms fruit having a striped red appearance with such stripes being particularly noticeable on the backside. Such striping is not clearly depicted in the photographs of U.S. Plant Pat. Nos. 5,937 and 7,146 (FIGS. 10 and 11). However, the striping is illustrated in the photographs showing typical fruit which is provided herewith for comparative purposes. On the contrary the fruit of the new variety exhibits the substantial absence of striping in all instances even on the backside. The fruits of the Daliguy (U.S. Plant Pat. No. 6,148) and Schneica (U.S. Plant Pat. No. 7,146) earlier reported mutations of the Jonagold variety are recognized to be significantly lighter in coloration than that of the new variety. Also, the fruit of the new variety colors approximately one week earlier than that of the Jonagold variety.

When representative fully ripened fruits of the Jonagold variety, the mutation of U.S. Plant Pat. No. 5,937, and the present variety were analyzed for color at the New York State Agricultural Experiments Station, Geneva, N.Y., using a Hunter Color Difference Meter the following results were recorded:

| | a | L |
|---|---|---|
| JONAGOLD variety | 11.4 | 50.6 |
| Mutation of United States Plant Patent No. 5,937 | 22.5 | 41.3 |
| RUBINSTAR variety | 30.4 | 37.2 |

The "a" meter reading provides a measure of redness with the higher the number being an indication of increasing red coloration. The Rubinstar variety exhibits the most red coloration. The "L" meter reading provides a measure of the hue since it detects mixtures of different colors and gives an indication of the purity of the red which is being observed. The Rubinstar variety exhibits the lowest number which confirms the purity of its red coloration.

Since the new variety exhibits a more intense coloring over more of the apple surface, the number of harvest pickings can be reduced to only one or two per season. Commonly 90 to 95 percent of the fruit crop can be harvested during the first picking thereby leaving only a relatively small quantity of fruit for a second harvest. On the contrary the mother Jonagold variety normally requires a greater number of harvest pickings. Accordingly, the new Rubinstar variety offers an economic advantage attributable to reduced labor costs in addition to the potential for earlier marketing and the formation of more attractive fruit.

I claim:

1. A new and distinct variety of apple tree which is a mutation of the Jonagold variety, substantially as illustrated and described, having the propensity to form fruit exhibiting a more intense red coloration which covers a greater portion of the fruit surface than its mother Jonagold variety, forms fruit which colors approximately one week earlier than its mother Jonagold variety, forms fruit having greater coloration than the earlier reported mutation of U.S. Plant Pat. No. 5,937 in the substantial absence of striping, forms fruit which is significantly darker in coloration than the earlier reported mutations of U.S. Plant Pat. Nos. 6,148 and 7,146, and exhibits a more compact growth habit than the mother Jonagold variety and its other previously reported mutations.

* * * * *